(12) United States Patent
Strobel et al.

(10) Patent No.: US 6,267,767 B1
(45) Date of Patent: Jul. 31, 2001

(54) INSTRUMENTARIUM AND METHOD FOR IMPLANTING A CRUCIATE LIGAMENT REPLACEMENT IN A KNEE JOINT

(75) Inventors: Michael Strobel, Mitterfels; Michael Sauer, Tuttlingen, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/343,387

(22) Filed: Jun. 30, 1999

(30) Foreign Application Priority Data

Nov. 6, 1998 (DE) .............................................. 198 51 152

(51) Int. Cl.⁷ ...................................................... A61B 17/88
(52) U.S. Cl. .............................. 606/104; 606/80; 606/84; 606/99; 606/102; 606/207; 604/60; 604/218
(58) Field of Search .................................. 606/72, 75, 79, 606/80, 86, 88, 99, 102, 104, 205, 207, 232; 604/15, 16, 18, 57, 59, 60, 159, 164.01, 164.12, 218, 220; 33/542, 555.1, 555.2, 544

(56) References Cited

U.S. PATENT DOCUMENTS

| | | | |
|---|---|---|---|
| 2,751,907 | * 6/1956 | Hickey | 604/60 |
| 3,993,045 | * 11/1976 | Ion | 600/481 |
| 4,566,466 | * 1/1986 | Ripple et al. | 606/102 |
| 4,790,819 | * 12/1988 | Li et al. | 604/59 |
| 4,801,263 | * 1/1989 | Clark | 433/90 |
| 4,963,144 | * 10/1990 | Huene | 606/73 |
| 5,741,267 | * 4/1998 | Jorneus et al. | 606/102 |
| 5,772,597 | 1/1998 | Goldberger et al. | 600/473 |
| 5,827,299 | 10/1998 | Thomason et al. | 606/148 |

* cited by examiner

*Primary Examiner*—David O. Reip
(74) *Attorney, Agent, or Firm*—St. Onge Steward Johnston & Reens LLC (57) ABSTRACT

An instrumentarium for implanting a cruciate ligament replacement in a knee joint comprises an applicator for inserting a peg into a bore in a bone into which bore the cruciate ligament is received. The peg is inserted into a clear space between said cruciate ligament replacement and a wall of the bore in the bone. The applicator comprises a hollow shaft open at its distal end, a push-rod disposed in said hollow shaft and an operating element connected to the push-rod for moving it between a first position with a distal end retracted into the hollow shaft allowing a peg to be inserted, and a second position for pushing the peg out of said distal open end.

27 Claims, 8 Drawing Sheets

INSTRUMENTARIUM AND METHOD FOR IMPLANTING A CRUCIATE LIGAMENT REPLACEMENT IN A KNEE JOINT

BACKGROUND OF THE INVENTION

1. Field of the Invention

The present invention relates to an instrumentarium and a method for implanting a cruciate ligament replacement in a knee joint.

Operations by which a cruciate ligament replacement is implanted in a knee joint are generally known in the art. Such operations become necessary in cases where the cruciate ligament in the knee is broken or has been heavily damaged in some other way. Today, one preferably uses endogenous materials as cruciate ligament replacements. Especially the patellar tendon or the semitendinosus tendon have proved to be suitable for use as a required cruciate ligament replacement.

2. Related Prior Art

A method and an instrumentarium for restoring the anterior cruciate ligament using one of such tendons as a cruciate ligament replacement has been known from EP-A-0 440 991.

If in the case of this known method the semitendinosus tendon is to be used as a substitute for the cruciate ligament, the tendon is initially removed with the aid of a tendon cutter, and is then cut to different segments or sections. Some of these segments are folded over in the form of a loop so that double sections are obtained. The individual segments and/or the double segments are then once more placed one beside the other, and their ends are connected by suture threads. The tendon bundle so obtained then forms the replacement for the cruciate ligament.

The cruciate ligament replacement is then fixed between the distal end of the femur and the proximal end of the tibia. To this end, one initially drills a through-bore in the proximal end of the tibia, and a blind bore or closed tunnel in the distal end of the femur, whereafter the ends of the cruciate ligament replacement are inserted into, and fixed in, the two bores, respectively.

Fixing the cruciate ligament replacement in the through-bore of the tibia is effected with the aid of a screw, according to EP-A-0 440 991. In contrast, for fixing the cruciate ligament replacement in the blind bore of the femur, it is stretched by means of suture threads, that are guided through a thin drilled passing channel forming an extension of the blind bore, and a button-like plate applied against an outer face of the femur opposite the blind bore.

If the operation has been successful, this purely mechanical method of fixing the cruciate ligament replacement in the two bores is reinforced, in the course of time, by the cruciate ligament replacement taking adhesion to the surrounding bone material. This adhesion then finally guarantees a durable and reliable hold for the cruciate ligament replacement in the knee.

However, it has been found that when implanted by that method the cruciate ligament replacement does not in all cases grow to the surrounding bone material as desired. This may happen in particular when the cruciate ligament replacement is retained too loosely in the receiving bore. For, in this case the cruciate ligament replacement tends to move with every, even very slight, movement of the knee so that an initial adhesion, that may have formed, is easily broken up again. Another, likewise frequently encountered cause for such difficulties lies in the fact that the cruciate ligament replacement as such has too little contact with the surrounding bone material.

This latter situation may arise in particular when the cruciate ligament replacement, as has been mentioned before, consists of segments folded over in the form of a loop. This is so because the maximum bending radii make the end of the cruciate ligament replacement, i.e. the area of the loop, larger than the area immediately beneath the latter. When the loop is then to be introduced into the blind bore of the femur in the usual way, it is the width of the loop that determines the size and/or the diameter of the blind bore. And this in turn leads to the situation that clear spaces remain below the loop between the cruciate ligament replacement and the walls of the blind bore. Due to such clear spaces, there is no contact between the cruciate ligament replacement and the surrounding bone material at these points, whereby any adhesion is rendered difficult or may even be prevented.

It is, therefore, an object of the present invention that the before-mentioned difficulties should be avoided. It is a further object of the invention to provide an instrumentarium for implanting a cruciate ligament replacement in a knee joint.

SUMMARY OF THE INVENTION

This can be achieved simply and very successfully by placing pegs in the clear spaces between the cruciate ligament replacement and the walls of the receiving bore, which pegs on the one hand fix the cruciate ligament replacement in the bore and on the other hand improve, or even establish, the contact between the cruciate ligament replacement and the walls of the bore.

Placing such pegs in a bore, in which a cruciate ligament replacement has been implanted before, requires however a suitable or, optimally, an even customized instrumentarium, as will be easily appreciated in view of the very limited space and restricted accessibility available in a knee joint. However, such an instrumentarium has not been known heretofore in the art, either.

According to the invention, an instrumentarium has an applicator for inserting a peg in a clear space between the cruciate ligament replacement and the wall of the bore, where the applicator comprises a hollow shaft that is open at its distal end and a push-rod guided in the hollow shaft, and where the applicator comprises an operating element by means of which the push-rod can be displaced in the hollow shaft so that a peg, previously introduced into the hollow shaft, can be pushed out through the opening at the distal end of the hollow shaft.

Using such an applicator it is possible to perform the two steps necessary for placing a peg in the described clear space, namely advancing the peg to a position near the clear space and pushing the peg into the clear space, in a controlled and safe way. This applies especially to arthroscopic interventions of the kind usual today in knee operations.

When using the applicator, the peg is initially introduced into the hollow shaft, whereafter the distal end of the hollow shaft is advanced to a position near the clear space in which the peg is to be placed. Only after the opening at the distal end of the hollow shaft has reached a suitable position at or before the clear space will the push rod be advanced in the direction of the distal end through the operating element inside the hollow shaft. This then allows the peg in the hollow shaft to be inserted in a controlled and purposeful way into the clear space between the cruciate ligament replacement and the surrounding wall of the bore.

Moving the peg to a position near the clear space by means of the hollow shaft in which it is received provides the advantage that the peg can be guided safely and purposefully even under the limited space conditions prevailing in the knee joint. By comparison with a pair of forceps, for example, or a similar instrument it is thus ensured that the peg cannot get lost in the knee joint due to inadvertent movements or if the peg should hit a bone.

Further, pushing the peg out of the hollow shaft by means of a push-rod that can be advanced by an operating element, provides the advantage that it is thus possible to exert upon the rear end of the peg, even during its insertion, a desired pressure as necessary to fix the peg as firmly as possible between the cruciate ligament replacement and the walls of the bore.

It is thus possible to position the peg purposefully and in a controlled way, in spite of the restricted place available and the limited accessibility of the respective clear space.

According to one embodiment of the invention, the hollow shaft of the applicator is curved.

This feature provides the advantage that as a result of this arrangement the point of the hollow shaft can be advanced more easily to the bore receiving the cruciate ligament replacement and, thus, to the clear space to be filled. The bore ends at the articular surface of the femur opposite the articular surface of the tibia. The described feature now makes it possible to approach the curved hollow shaft of the applicator laterally to the opening of the bore.

According to a further development of the feature described before, the hollow shaft is curved regularly over its length.

This feature provides the advantage that due to the regularity of the curvature the push-rod can be displaced inside the hollow shaft easily and, above all, without jerks. This is an advantage with respect to the controlled insertion of the peg.

According to an alternative embodiment of the feature described before, the hollow shaft of the applicator is substantially straight at least over its central section, and is then bent off in one direction near its distal end.

This feature provides the advantage that while there is a curvature in this case that facilitates the advancing movement of the applicator toward the clear space, the operator's vision of the clear space is at the same time less obstructed by the instrument in this case.

According to a further alternative embodiment, the hollow shaft of the applicator is straight over its full length.

This feature provides the advantage that it permits the pushrod to be displaced inside the hollow shaft without any obstruction. This means that little frictional resistance is opposed to the push-rod in this case, which improves the operating properties of the applicator generally.

According to a further embodiment of the beforementioned features, the push-rod comprises a thicker section at its distal end and a thinner central section over a length section. The outer diameter of the thicker section corresponds to the clear inner diameter of the hollow shaft. The outer diameter of the thinner central section being smaller than the outer diameter of the thicker section.

This feature provides the advantage that due to its thinner central section, the push-rod is very flexible so that it can adjust itself easily to a curvature of the hollow shaft. As a result, the push-rod can be displaced inside the hollow shaft even more easily and with lesser jerks. At the same time, due to the thicker section at the distal end of the push-rod, this feature provides the advantage that any peg placed in the hollow shaft will be subjected to the action of a pushing element that fills the entire hollow shaft with the result that the peg is guided more uniformly and with better control and is safely prevented from tilting or jamming in the hollow shaft. All in all, this feature thus improves the controlled ejection of the peg from the hollow shaft.

According to a further embodiment of the invention, the distal end of the push-rod can be displaced between a first and a second position. In the first position, the distal end of the rod being retracted into the hollow shaft from the opening of the hollow shaft corresponding to the length of the peg. In its second position, the distal end of the push-rod projects beyond the opening of the hollow shaft.

This feature provides the advantage that the peg can be safely held over its entire length in the hollow shaft. When pushing out the push-rod, the peg can be ejected fully from the hollow shaft, i.e. over its full length. This ensures that after ejection of the peg and during withdrawal of the applicator, the peg will not get displaced inadvertently in the clear space, or be fully pulled back from the latter. This latter condition may occur in particular if the peg should adhere to the material of the hollow shaft, for example due to tissue particles or due to adhesive forces. In addition, this feature provides the advantage that the peg can be pushed very deep, and with sufficient pressure, into the clear space already during its insertion into the clear space.

According to a further embodiment of the invention, the operating element can be operated along an operating axis, and a cross-section plane of the opening of the hollow shaft is arranged at an angle $\alpha$ of less than 90°, preferably between 0° and 45°, related to the operating axis.

This feature must be regarded especially in connection with the insertion of a peg into the blind bore in the femur. In this case, the peg must be approached to the clear space, that is to receive the peg, from below or at least obliquely from below. At the same time, the lower surface of the femur is accessible to a limited extent only. By way of illustration, this feature means that the direction, along which the peg leaves the hollow shaft, is inclined relative to the operating axis of the applicator, and this in the particularly preferred case at a right angle. This advantageously facilitates the action of approaching the peg to the clear space in which it is to be placed.

According to a further embodiment of the invention, the operating element of the applicator comprises a handle at the proximal end of the push-rod, preferably a ring that can be actuated by the thumb, and a counter-handle on the hollow shaft.

This feature provides the advantage that it permits the operator to act directly on the push-rod in order to push the peg out of the hollow shaft. This gives him a better feeling of the peg, as compared to a case where the peg would be connected with the operating element through additional connection elements. The counter-handle on the hollow shaft, in combination with the handle at the proximal end of the push-rod, provides the advantage that the applicator can thus be operated easily with one hand. The preferred embodiment of the handle in the form of a ring provides the advantage that it allows the operator, without the need to change his grip, to move the push-rod also in the opposite direction, i.e. to withdraw it if necessary, for example in order to adjust the position of the peg in the clear space in which it is to be received. In addition, the described features are very simple, from a constructional point of view, so that a corresponding applicator can be produced at low cost.

Further, the comparatively simple design also permits easy sterilization of the applicator after use.

According to a further embodiment of the invention, the pushrod can be fully withdrawn from the hollow shaft of the applicator.

This feature also serves to permit easy and thorough sterilization of the applicator, and provides the advantage that both the hollow shaft and the push-rod guided in it are easily accessible during sterilization.

According to a further embodiment of the invention, the applicator comprises a releasable locking mechanism, for fixing the push-rod relative to the hollow shaft.

This feature provides the advantage that the push-rod can be locked in its position relative to the hollow shaft, whereby it is prevented from falling off unintentionally. However, this feature also provides the advantage that during the phase in which a peg placed in the hollow shaft is to be approached to the clear space, the push-rod cannot be displaced inadvertently, whereby the peg might be pushed out of the hollow shaft unintentionally. Thus, this feature also contributes toward preventing errors or mishaps that might have serious consequences.

According to a further development of the feature described before, the locking mechanism comprises a spring-biased lever, whose end carries a lug that engages an annular groove in the push-rod in the locked condition.

Such a locking mechanism is on the one hand very simple under constructional aspects and guarantees on the other hand sufficiently reliable functioning. The simple structure of the locking mechanism further enhances the sterilization properties of the system. And at the same time, it also reduces the production costs of the applicator. Further, such a locking mechanism is easy to operate by the operator, which advantageously helps prevent errors during operation.

According to a further development of the invention, the instrumentarium comprises a plurality of applicators with different inner diameters.

This feature provides the advantage that an exactly fitting and, thus, an optimally suited applicator is available for each of a number of pegs of different sizes. As will be explained hereafter in further detail, the different peg sizes are due to the fact that the pegs to be inserted should advantageously be optimally adapted to the clear spaces in which they are to be received, and to their respective space conditions.

According to a further development of the invention, the instrumentarium comprises a plurality of metering rods for determining the size of the clear space, the distal end of each metering rod corresponding substantially to the shape of the peg to be inserted and the end diameters of the metering rods being different one from the other.

Determining the size of the clear space into which the peg is to be inserted is effected with the aid of these metering rods in a simple way, by introducing initially the proximal end of one of the metering rods into the clear space. The end diameter of that metering rod then gives the operator a comparative measure of the size of the clear space. The size of the clear space can be determined more exactly by introducing further metering rods, with different end diameters, into the clear space to be measured. The end diameter of that metering rod that fits optimally into the clear space, then provides the measure for the required diameter of the peg to be inserted.

Supplementing the instrumentarium according to the invention by such metering rods therefore provides the advantage that it is now possible to determine the size of the clear space and, thus, the size of the required peg in a very easy, yet exact fashion. This is an advantage especially if one considers that the peg must be introduced at a certain pressure into the clear space between the cruciate ligament replacement and the walls of the bore in order to block the cruciate ligament replacement in the bore as firmly as possible. Given the fact, however, that the cruciate ligament replacement as such has a certain elasticity, the clear space will be additionally enlarged by that pressure. This fact is automatically allowed for when determining the size of the clear space with the aid of the described metering rods, as the latter can also be introduced into the clear space with the necessary pressure. In addition, the metering rods according to the invention can be sterilized easily and thoroughly.

According to one development of the previously described feature, each metering rod is provided at its distal end with at least one visible mark, arranged at a certain distance from the end of the metering rod.

This feature provides a scale that permits to determine the depth of the clear space, i.e. the length of the peg to be inserted. During insertion of the metering rod into the clear space, the visible mark can be easily observed with the aid of the camera, which is normally used in arthroscopic operations, or with the aid of an endoscope.

According to a further embodiment of the invention, the instrumentarium additionally comprises at least one tamping tool by means of which the peg can be pressed into the clear space.

This feature provides the advantage that once the peg has been inserted into the clear space with the aid of the applicator, it can be blocked in the clear space with considerably higher pressure. The higher pressure, that can be applied by the tamping tool as compared with the applicator, results mainly from the fact that the push-rod of the applicator has a certain flexibility for the reasons explained above. This flexibility is, however, not necessary for the tamping tool so that much more force can be applied on the peg by the tamping tool.

According to a further development of the feature described before, the tamping tool is provided with a dished impact surface at its distal end.

This feature provides the advantage that as the peg is pressed into the clear space, it will automatically center itself relative to the impact surface of the tamping tool so that the tamping tools acts to transmit the force optimally to the peg. And the risk that the tamping tool may slide off the peg during the pressing action is also reduced.

According to a further development of the two features described before, the tamping tool is provided with a visible mark at its distal end, at a given distance from the impact surface.

This feature provides the advantage that this mark makes it easier to see how far the peg has been introduced into the clear space, that had been measured before with the aid of the metering rods. Thus, it is now possible to decide if the peg should be pressed further into the clear space, or if it already occupies the desired end position.

According to a further development of the features described before, the instrumentarium comprises a plurality of tamping tools with different end diameters.

This feature provides the advantage that optimally adapted tamping tools are now available for pegs of different sizes, and the related different space conditions. This makes it possible to block the pegs optimally in the clear space between the cruciate ligament replacement and the walls of the bore receiving it, regardless of their respective size.

According to further embodiment of the invention, the instrumentarium comprises pressure forceps by means of which the peg can be shaped.

This feature is based on the idea that the peg to be inserted should advantageously consist of endogenous material. A material particularly well suited for this purpose is the spongiosa obtained when drilling the blind bore and the through-bore intp the femur and the tibia. With the aid of the pressure forceps the spongiosa can very well be given the shape of the peg to be inserted.

According to a further development of the feature described before, the jaws of the pressure forceps enclose between them in the closed condition an elliptic or circular opening.

This feature provides the advantage that shaping the peg to be inserted is thus facilitated. Especially, it is now possible in a simple way to compress the bone material to an elliptic or circular shape until the desired diameter of the peg to be inserted is obtained.

According to a further development of the features described before, the jaws of the pressure forceps enclose between them in the closed condition a cylindrical or conical opening.

This feature provides the advantage that the opening thus corresponds to the entire contour of the peg to be inserted. By way of illustration, it is thus possible to bring the bone material into the desire shape solely by compressing it between the jaws of the pressure forceps.

According to a further embodiment of the invention, the instrumentarium comprises a hollow chisel or a core drill by means of which the bone material can be removed for shaping the peg.

This feature takes up the before-mentioned embodiment of the invention, in that it enriches the instrumentarium by the possibility to gain bone material. Compared with synthetic pegs, i.e. pegs made from non-endogenous material, the pegs made from such material offer the advantage that they tend to grow much more easily and quickly to the cruciate ligament replacement, which also preferably consists of endogenous material, and to the femur and tibia. In addition, introducing synthetic materials, especially into a joint, is also connected with an increased risk of infection. This risk of infection is likewise reduced by the use of pegs made from bone material.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

Certain exemplifying embodiments of the invention are shown in the drawings and will be explained in more detail in the description below. In the drawings.

DETAILED DESCRIPTION OF PREFERRED EMBODIMENTS

As will become apparent from the description of the Figures that follows, individual steps of the method according to the invention will also be described hereafter in connection with the detailed explanation of the instrumentarium according to the invention.

Figure 1:
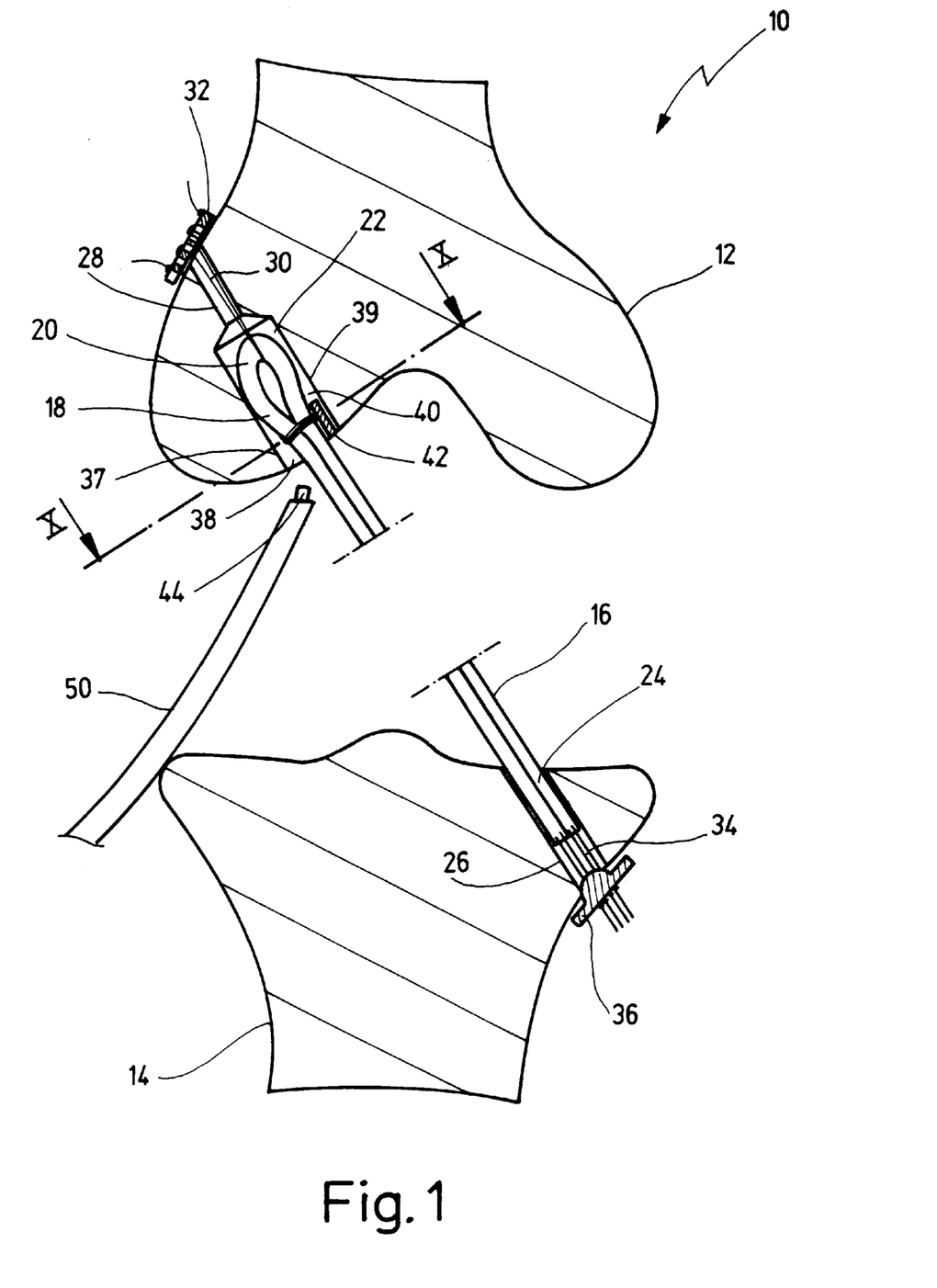
FIG. 1 shows a diagrammatic cross-section through a knee joint with a cruciate ligament replacement.

In FIG. 1, a knee joint shown diagrammatically is indicated generally by reference numeral 10.

The knee joint 10 forms the connection between the distal end of the femur 12 and the proximal end of the tibia 14. Between the two, which for the sake of clarity are illustrated at an out-of-scale distance, one relative to the other, there can be seen a cruciate ligament replacement 16. The proximal end 18 or the cruciate ligament replacement 16 is formed to a loop 20. The loop 20 is inserted in a blind bore 22, for fastening the cruciate ligament replacement 16 on the femur 12.

The distal end 24 of the cruciate ligament replacement 16 is positioned in a through-bore 26 that has been drilled into the proximal end of the tibia.

The end of the blind bore 22 in the femur 12 is followed by a thin drilled passing channel 28 through which a thread 30 is passed. The thread 30 is fixed by means of a plate 32 against the outside of the femur 12 opposite the blind bore 22 and exerts a pull on the loop 20 of the cruciate ligament replacement 16. This fixes the cruciate ligament replacement 16 at the distal end of the femur 12.

The distal end 24 of the cruciate ligament replacement 16 is similarly fixed in the through-bore 26 in the proximal end of the tibia 14, by means of one or more threads 34 and a plate 36. The threads 30, 34 as such are suture threads of the kind well-known and customarily used in the art.

Below the top end of the loop 20, there remains a clear space 38 between the cruciate ligament replacement 16 and the wall section 37 of the blind bore 22. This clear space 38 necessarily results from the fact that the loop 20 occupies more space in the area of its top end than below the latter.

Likewise, a clear space 40 remains between the wall section 39 of the blind bore 22 and the cruciate ligament replacement 16.

According to the method underlying the invention, pegs 42 and 44, respectively, are inserted into the clear spaces 38, 40. The pegs 42, 44 consist in this case of endogenous bone material, i.e. the spongiosa obtained when drilling the blind bore 22 and the through-bore 26. In the representation of FIG. 1, the peg 42 is already located in the clear space 40, whereas the peg 44 is just being placed in the clear space 38 by means of an applicator 50.

Figures 2, 3, 4:
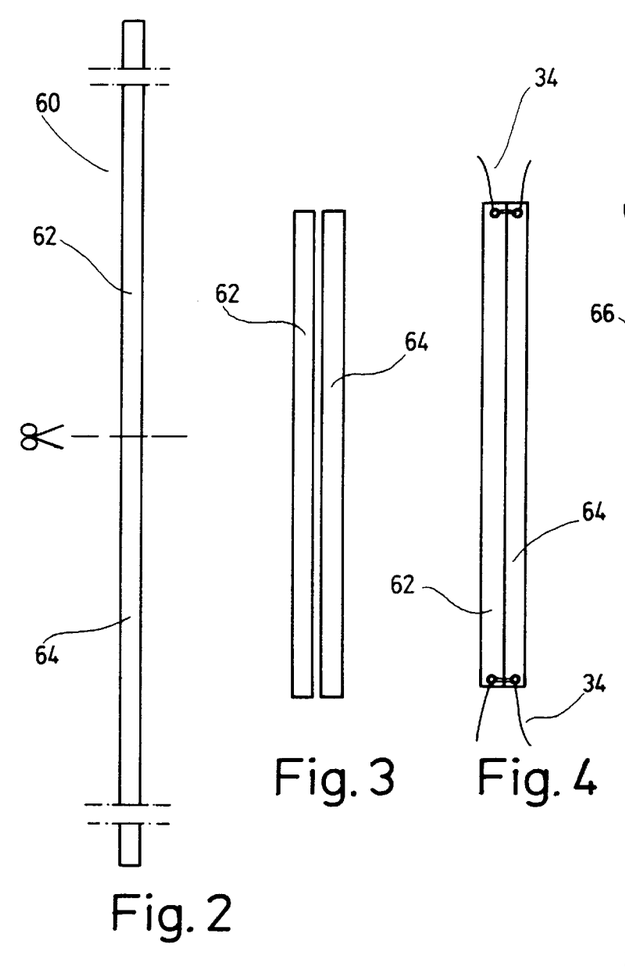
FIGS. 2 to 5 show different steps of preparing a cruciate ligament replacement from the semitendinosus tendon.
Figure 5:
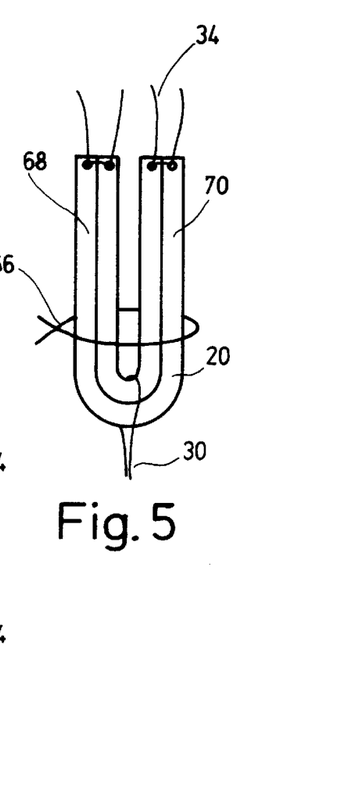

Folding over the cruciate ligament replacement 16 to form the loop 20 is effected usually as part of the process of making the cruciate ligament replacement 16 from the semitendinosus tendon. For this purpose, one initially removes at least part, frequently the central third, of the semitendinosus tendon. According to FIG. 2, that section 60 of the semitendinosus tendon is then cut to segments 62, 64 of approximately equal length. As can be seen in FIGS. 3 and 4, the segments 62, 64 are then placed one beside the other and connected at their ends by means of threads 34. Thereafter, the connected sections 62, 64 are folded over to form the loop 20, which preferably is then tied up about its legs 68 and 70 by an additional thread 66. Finally, the thread 30 is threaded through the opening of the loop 20 so that the cruciate ligament replacement 16 can be fixed in the blind bore 22 in the femur by means of that thread 30.

Figure 6:
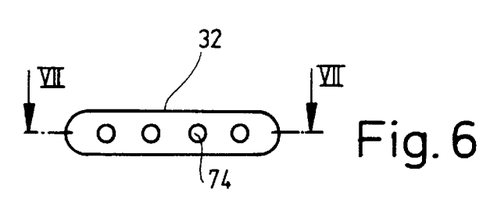
FIG. 6 shows a top view of a plate that serves for fixing the cruciate ligament replacement in the femur.
Figure 7:
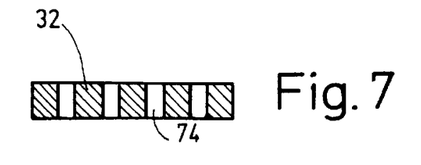
FIG. 7 shows a cross-sectional view of the plate of FIG. 6, along line VII—VII.

The plate 32, that serves this purpose as shown in FIG. 1, is configured in this case as an oblong plate with a total of four holes 74 arranged at equal spacings one from the other, as can be seen in FIGS. 6 and 7, respectively. In order to fix the cruciate ligament replacement 16 in the blind bore 22, the ends of the thread 30 are threaded through the holes 74 alternately from the top and from the bottom, and are then knotted under tension. The plate 32 thus forms an anchor by means of which the cruciate ligament replacement 16 is fixed in its position.

Figure 8:
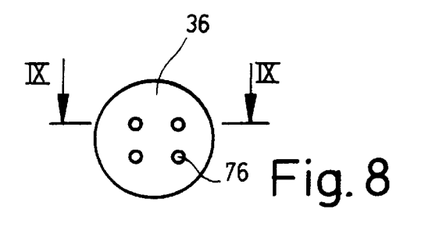
FIG. 8 shows a top view of another plate that serves for fixing the cruciate ligament replacement on the tibia.
Figure 9:
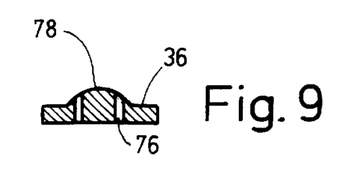
FIG. 9 shows the cross-sectional view of the plate of FIG. 8, along line IX—IX.

The plate 36, that serves to fix the cruciate ligament replacement 16 in the proximal end of the tibia 14, has a circular, button-like shape, as can be seen in FIGS. 8 and 9. It comprises four holes 76, arranged in square configuration, as well as a central elevation 78. As appears from the representation of FIG. 1, the elevation 78 serves to center the plate 36 relative to the through-bore 26. As a result of this arrangement, the plate 36 is seated free from play relative to the throughbore 26.

In the described embodiment, the plates 32 and 36 are preferably made from titanium. According to an alternative embodiment, the distal end 24 of the cruciate ligament replacement 16 may, however, also be fixed in the tibia 14 by means of a screw, instead of the plate 36.

Figure 10:
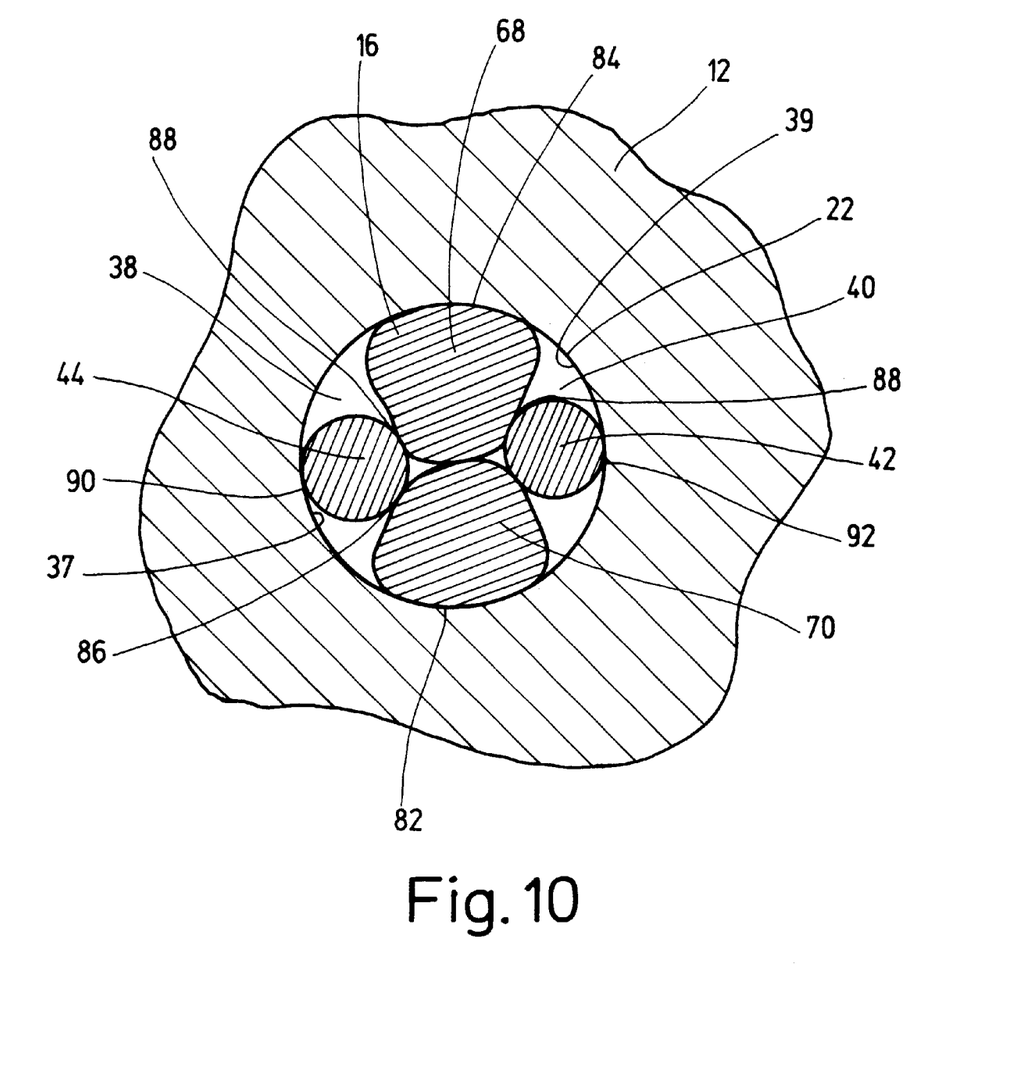
FIG. 10 shows a cross-sectional view of the cruciate ligament replacement inserted in the femur, along line X—X in FIG. 1.

The cross-sectional view of FIG. 10 illustrates how the pegs 42, 44 are positioned in the clear spaces 38, 40 for improving the fit of the cruciate ligament replacement 16 in the blind bore 22 of the femur 12. The diameter of the blind bore 22 is sized to correspond substantially to the width of the loop 20. This already provides natural contact points 82, 84 between the legs 68, 70 of the loop 20 and the wall sections 37, 39 of the blind bore 22. And of course the areas of contact of the contact points 82, 84 increase the more the cruciate ligament replacement 16 is compressed in the blind bore 22.

By inserting the pegs 42, 44 into the clear spaces 38, 40, as provided for by the invention, one achieves on the one hand that the legs 68, 70 of the cruciate ligament replacement 16 are additionally urged radially to the outside. This already has the result to increase the contact areas of the contact points 82, 84. On the other hand, however, additional contact points 86, 88 and 90, 92 are produced between the inserted pegs 42, 44 and the legs 68, 70 of the cruciate ligament replacement 16, and between the pegs 42, 44 and the walls 37, 39 of the blind bore 22.

As the pegs 42, 44 of the illustrated embodiment are made from endogenous bone material, they will very easily grow to the likewise endogenous material of the cruciate ligament replacement 16 and the femur at the additional contact points 86, 88 and 90, 92. Thus, the hold of the cruciate ligament replacement 16 in the blind bore 22 improves, both at short sight, after insertion of the pegs 42, 44 and at long sight, after the before-mentioned elements have grown together, as the size of the contact areas of the contact points 82, 84, 86, 88, 90, 92 increases.

The pegs 42, 44 therefore serve a dual function, namely on the one hand to fix the cruciate ligament replacement 16 better in the blind bore 22 immediately after the operation and on the other hand, in the long run, to provide additional and larger contact areas to support the natural adhesion of the cruciate ligament replacement 16 in the blind bore 22.

In the method underlying the present invention, the size of the pegs 42, 44 is advantageously adapted to the size of the clear spaces 38, 40. From that it results that both the length and the diameter of the pegs 42 and 44 may be different.

Hereafter, a preferred embodiment of an instrumentarium according to the invention will be described, which must of course be adapted as optimally as possible to the described application, considering the limited space available in a knee joint 10.

The most important component of the preferred instrumentarium is an applicator that serves to advance the pegs 42, 44 to the clear spaces 38, 40 and to insert them into the latter. An applicator, which is optimized with respect to these two functions, is indicated generally by reference numeral 50 in FIG. 11.

Figure 11:
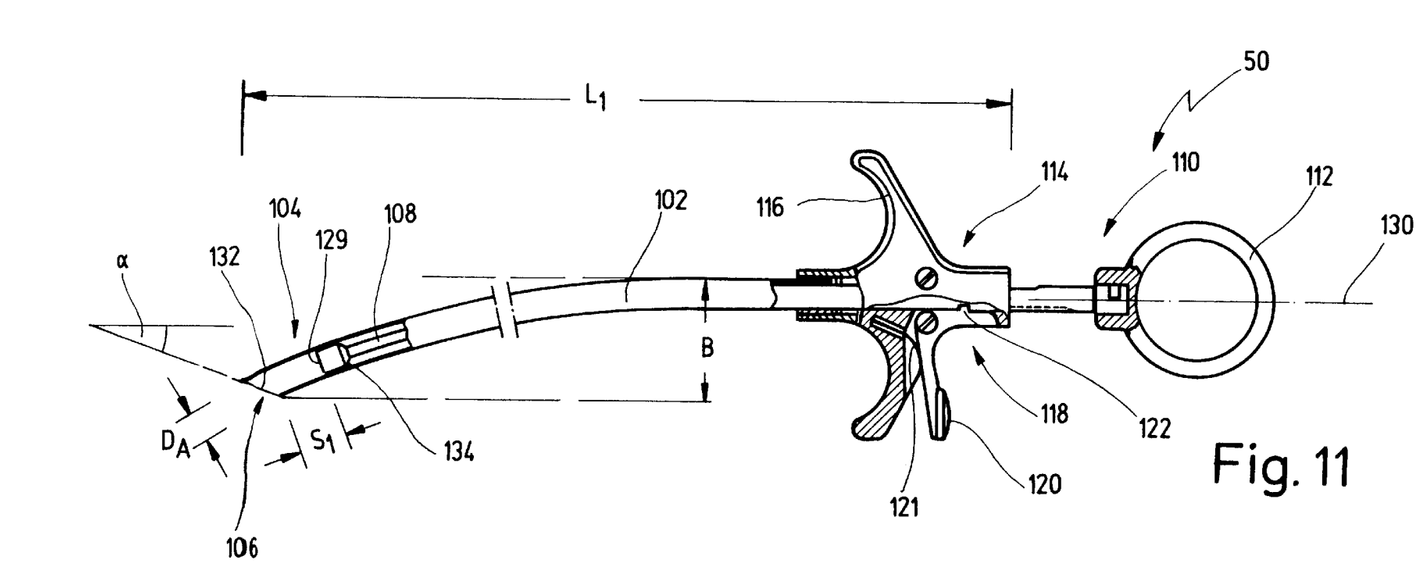
FIG. 11 shows a preferred embodiment of the applicator according to the invention, partly cut away.

The applicator 50 comprises a curved hollow shaft 102 with an opening 106 at its distal end 104. Located inside the hollow shaft 102 is a removable push-rod 108, which is fully depicted in FIG. 12.

Figure 12:
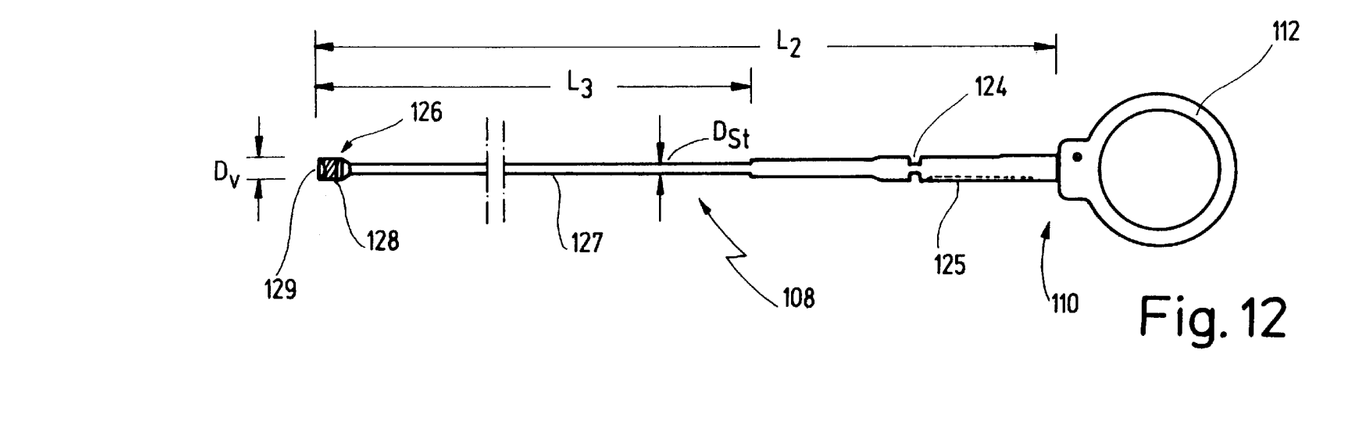
FIG. 12 shows the push-rod of the applicator of the invention as shown in FIG. 11.

At its proximal end 110, the push-rod 108 carries a handle 112, in the present case a ring handle. The proximal end 114 of the hollow shaft 102 carries a respective counter-handle 116. In operation, the counter-handle 116 of the hollow shaft 102 is preferably gripped by the index finger and middle finger of one hand, while for actuating the push-rod 108 the thumb of the same hand is passed through the ring handle 112. This allows the applicator 50 to be held by one hand, and the push-rod 108 to be simultaneously advanced or withdrawn, as needed, by the same hand.

In addition, the applicator 50 comprises a locking mechanism 118. The locking mechanism 118 includes a pivoting lever 120 which is biased by a spring 121 bearing against the counterhandle 116. At its pivoting end, the lever 120 carries a lug 122 that serves for locking the push-rod 108, for which purpose it engages an annular groove 124 provided thereon.

In the released condition of the locking mechanism 118, the push-rod 108 can be fully withdrawn to the rear from the hollow shaft 102. This may be useful in the first line if the applicator 50 is to be sterilized following an operation, as all parts of the applicator 50 are then easily accessible.

Conversely, the push-rod 108 can be pushed forward in the hollow shaft 102, after the locking mechanism 118 has been released. In this case, the lug 122 then slides into a lengthwise groove 125 arranged in the proximal end section of the push-rod 108.

The overall length $L_1$ of the hollow shaft 102 of the applicator 50 is 205 mm in the present embodiment. The curvature of the hollow shaft 102 is selected in such a way that the opening 106 is laterally offset from the proximal end 114 by approximately 60 mm. This means that the dimension B in the drawing is approximately 60 mm.

The overall length $L_2$ of the push-rod 108, measured from the distal end 126 to the stop of the handle 112, amounts to 220 mm in the present embodiment. Over that length $L_2$, the push-rod 108 is substantially composed of three functional sections.

One of such functional sections is formed by the distal end 126, which is followed by a central section 127 as second functional section. The distal end 126 of the push-rod 108 takes the form of a thicker section 128, whose outer diameter $D_V$ corresponds substantially to the clear inner diameter $D_A$ of the hollow shaft 102. In contrast, the central section 127 has a smaller outer diameter $D_{St}$. The third functional section of the push-rod 108 is located at the proximal end 110 and comprises both the handle 112 and that part of the push-rod 108 that forms the locking mechanism 118 together with the lever 120.

The length $L_3$ of the central section 127, including the thicker section 128, is 160 mm in the present embodiment. Die diameter $D_{St}$ of the central section 127 amounts to approximately 3 mm. The diameter $D_A$ of the illustrated applicator 50 is 5 mm. These dimensions have proved to be well suited for the intended application.

The thicker section 128 is provided at its distal end with an impact surface 129, which is dished in the illustrated embodiment. This ensures that a peg 42, 44 to be inserted into the clear spaces 38, 40 will be automatically centered relative to the impact surface 129.

Reference numeral 130 designates an operating axis of the applicator 50. This axis is the one along which the proximal end 110 of the push-rod 108 can be displaced by the operator in order to insert a peg 42, 44 into one of the clear spaces 38, 40. The operating axis 130 and the opening cross-section 132 of the opening 106 of the hollow shaft 102 enclose between them an angle α, in the illustrated embodiment of approximately 20°. The smaller the angle α, the larger is the offset between the direction in which the peg 42, 44 exits from the opening 106, and the operating axis 130. This makes it easier for the operator to insert the peg 42, 44 through an opening in the knee joint 10, which is accessible from the front, into the downwardly opening blind bore 22 in the femur 12.

In the operating position illustrated in FIG. 11, the push-rod 108 occupies a first position 134 in the hollow shaft 102, in which its distal end 126 is fully received in the hollow shaft 102. The impact surface 129 of the push-rod 108 is in this case spaced from the opening 106 of the hollow shaft 102 by a distance $S_1$. At the same time, the locking mechanism 118 is locked in this operating condition, i.e. the lug 122 is engaged in the annular groove 124 of the push-rod 108. Due to the distance $S_1$, the applicator 50 is thus in a position to substantially accommodate a peg 42, 44 to be inserted in the point of the hollow shaft 102. This guarantees that the peg 42, 44 to be inserted can be advanced to the clear space 38, 40 safely and without the risk of getting lost.

Figure 13:
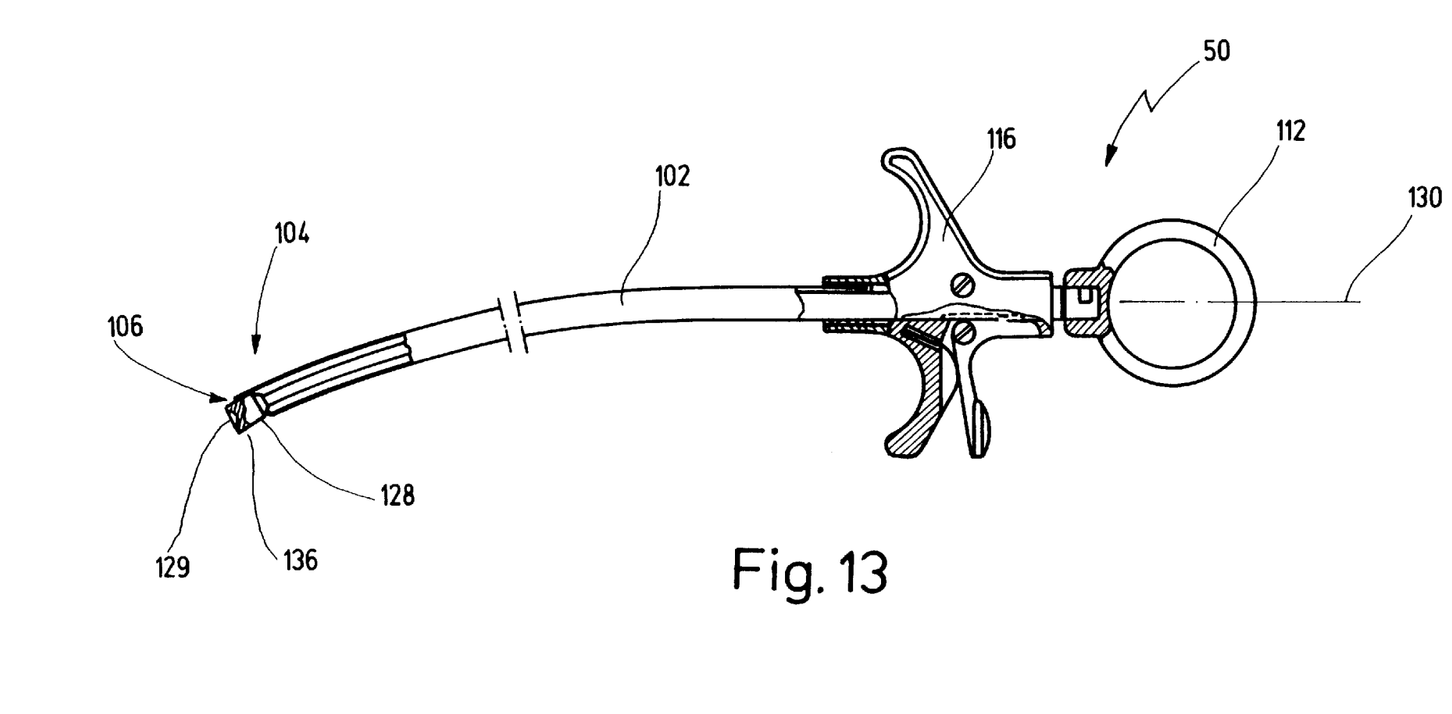
FIG. 13 shows the applicator of FIG. 11, in a second operating position.

In the operating position illustrated in FIG. 13, the thicker section 128 of the push-rod 108 occupies a second position 136 in which it projects beyond the opening 106 of the hollow shaft 102. This is the case when the push-rod 108 has been pushed into the hollow shaft 102 of the applicator as far as possible. The lug 122 of the locking mechanism 118 is located at the proximal end of the lengthwise groove 125 in that operating position. Due to the fact that the impact surface 129 of the push-rod 108 projects in this operating position beyond the distal end 104 of the hollow shaft 102, it is possible to push a peg 42, 44 to be inserted fully out of the hollow shaft 102 and to press it with the aid of the applicator 50 into the clear space 38, 40 a sufficient length to ensure that it cannot possible drop out by itself when the applicator 50 is withdrawn.

According to an alternative embodiment not shown in the drawings, the hollow shaft of the applicator exhibits an initial straight section, starting from the proximal end, and is curved in one direction only in the neighborhood of its distal end. The shape of the hollow shaft corresponds in this case substantially to the shape of the tamping tool that will be described hereafter.

Figure 14:
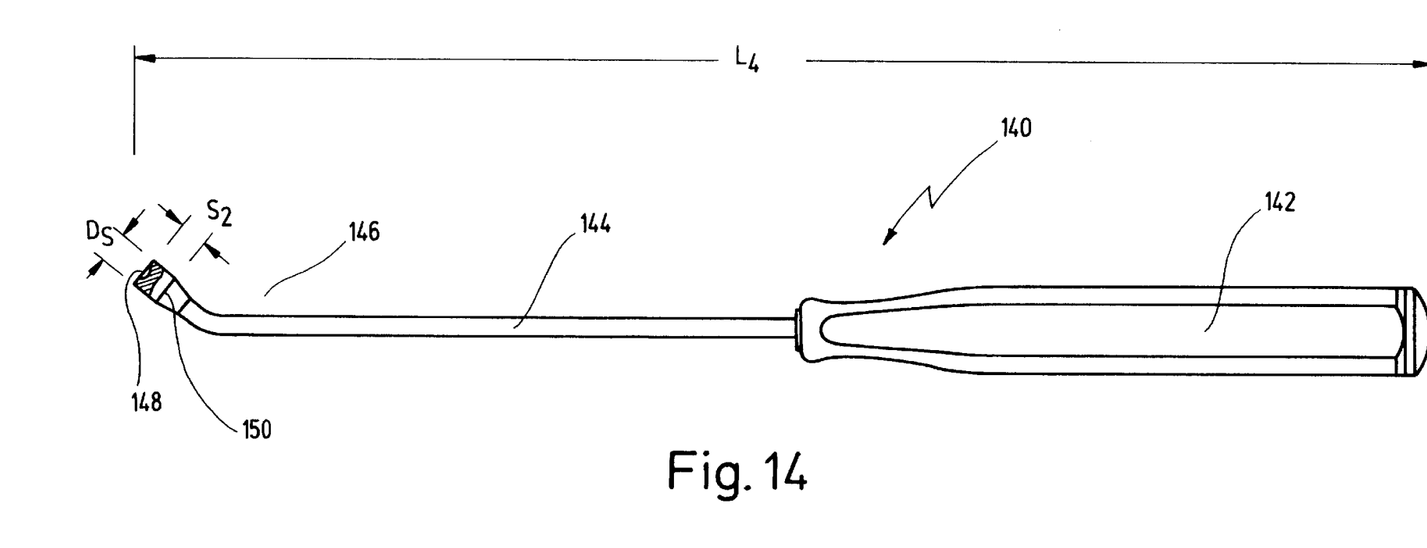
FIG. 14 shows a preferred embodiment of the tamping tool according to the invention.

In FIG. 14, a tamping tool supplementing the instrumentarium according to the invention is indicated generally by reference numeral 140.

The tamping tool comprises a handle 142 as well as a robust shaft 144 made from metal. Its overall length $L_4$ amounts to 275 mm in the described embodiment.

The distal end 146 of the tamping tool 140 is bent off at an angle of approximately 45°, and is equipped with an impact surface 148 which exhibits a dished configuration, for the same reasons as the impact surface 129 of the push-rod 108 of the applicator 50. The diameter $D_S$ of the impact surface 148 is likewise 5 mm in the case of the illustrated tamping tool 140. Preferably, however, the instrumentarium according to the invention comprises a plurality of tamping tools 140 with different end diameters $D_S$. This then permits an optimally adapted tamping tool 140 to be selected for pressing the peg 42, 44 into clear spaces 38, 44 of different sizes.

In the illustrated embodiment, the distal end 146 of the tamping tool 140 is provided with a mark 150, located at a distance $S_2$ from the impact surface 148. This mark 150 allows the operator to estimate the depth which the peg 42, 44 to be inserted has already been pushed into the respective clear space 38, 40. The operator can then decide if in the particular case he should push the peg 42, 44 further into the clear space 38, 40, by applying still greater forces.

Figure 15:
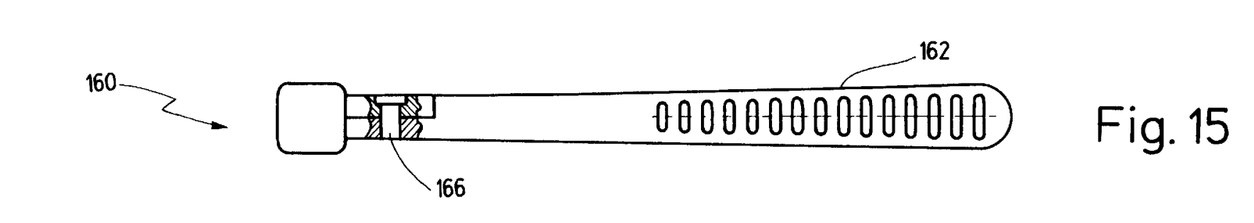
FIG. 15 shows a side view of one embodiment of the pressure forceps according to the invention.
Figure 16:
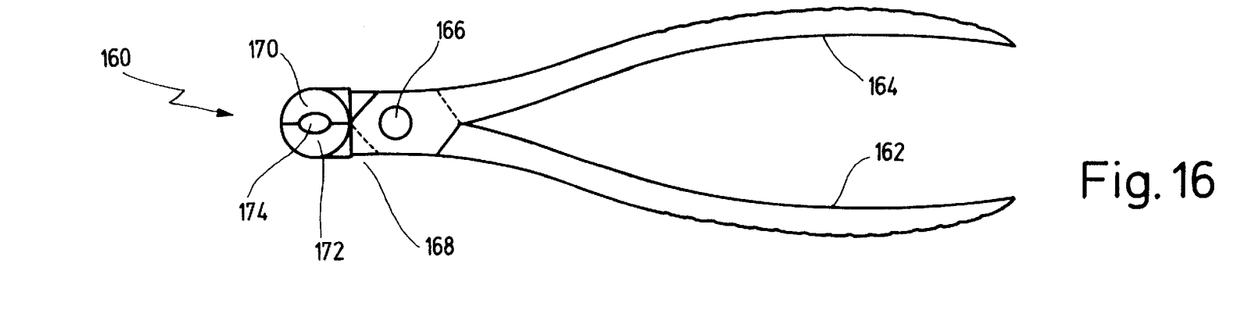
FIG. 16 shows a top view of the pressure forceps of FIG. 15.

In FIGS. 15 and 16, a pair of pressure forceps supplementing the instrumentarium according to the invention is indicated generally by reference numeral 160. The pressure forceps 160 comprise two halves 162, 164 that are pivotally connected in the conventional way by a hinge pin 166. Each of the two halves 162, 164 carries on its distal end 168 a jaw 170, 172 which when in contact one with the other, i.e. in the closed condition of the pressure forceps 160, enclose between them an—in this case—ellipse-shaped cylindrical opening 174. Alternative embodiments of the pressure forceps 160 may however also exhibit circular cylindrical or conical openings 174.

In the case of the method underlying the present invention, the pressure forceps 160 serve to shape pegs 42, 44 from bone material that can be obtained from drilling the blind bore 22 or the through-bore 26 into the femur 12 or the tibia 14, respectively, using a hollow chisel or core drill not shown in the drawing. For this purpose, the bone material obtained, especially the white spongiosa, is compressed by the pressure forceps to the desired shape.

Figure 17:
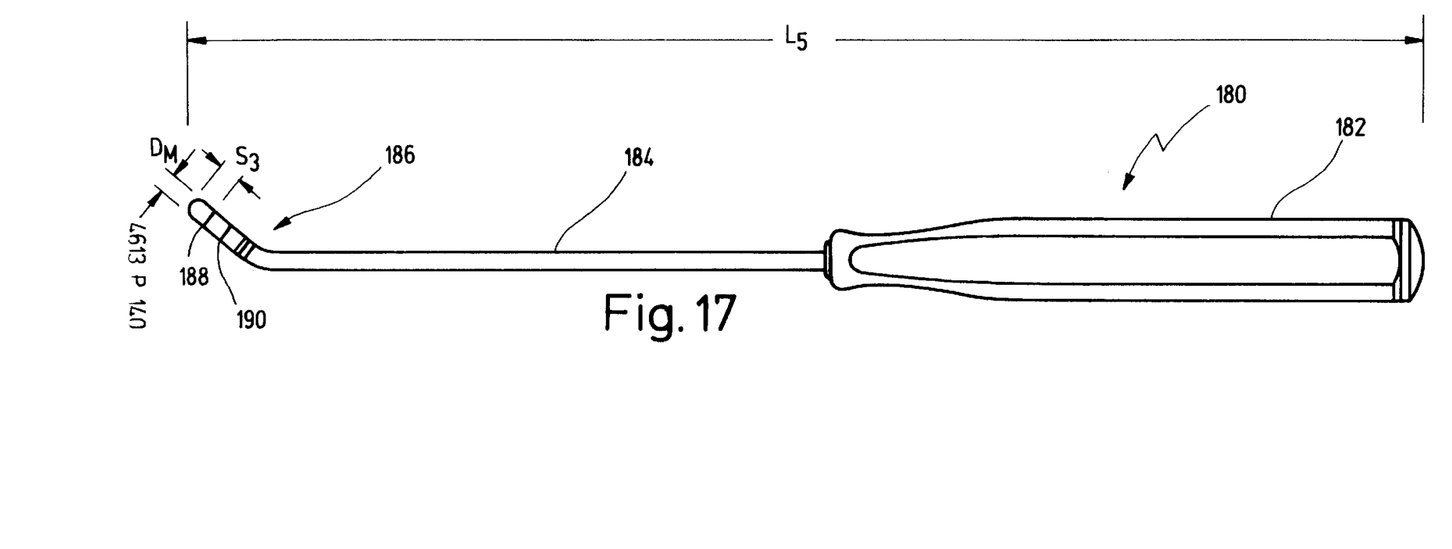
FIG. 17 shows a preferred embodiment of a metering rod according to the invention.

In FIG. 17, a metering rod supplementing the instrumentarium according to the invention is indicated generally by reference numeral 180.

The metering rod 180 comprises a handle 182 and a rigid rod 184 made from metal. Its overall length $L_5$ amounts again to 275 mm. The distal end 186 of the metering rod 180 corresponds substantially to the shape of the peg 42, 44 to be inserted, and is bent off, just as the distal end 186 of the tamping tool 140, at an angle of approximately 45°. This makes it easier for the operator to introduce the distal end 146 into the clear space 38, 40 for determining the size of that clear space. The distal end 186 of the metering rod 180 is regularly rounded, especially to ensure that the cruciate ligament replacement 16 will not be damaged when determining the size of the clear space 38, 40.

The end diameter $D_M$ of the distal end 186 of the metering rod 180 amounts to 4 mm in this case. As has been indicated already at the outset, the instrumentarium according to the invention comprises however several metering rods 180 with different end diameters $D_M$. By testing different metering rods the operator can thus determine in a simple way the size of the clear space 38, 40 and, consequently the required size of a peg 42, 44 to be inserted.

The metering rod 180 of the described embodiment carries a total of three marks 188, 190 on its distal end, by which the operator can judge the depth of the respective clear space 38, 40 within the blind bore 22. To this end, the marks 188, 190 are arranged at known distances $S_3$ from the end of the metering rod 180.

Figure 18:
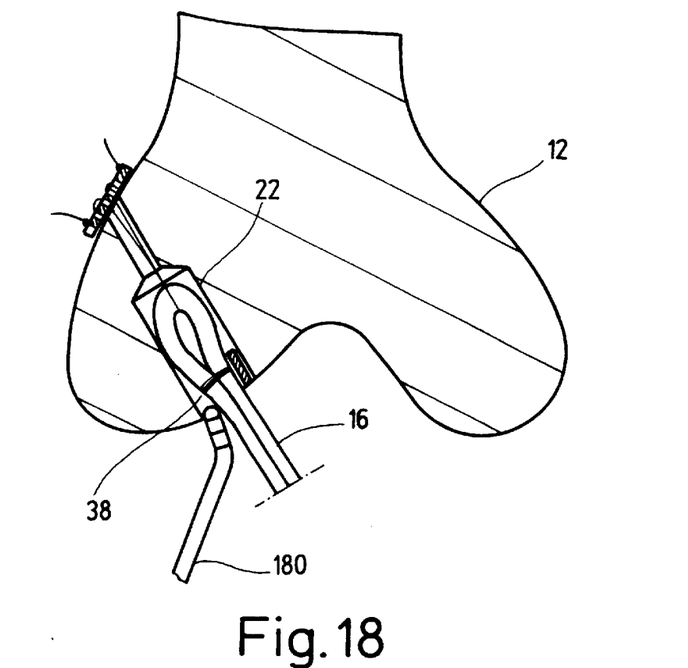
FIG. 18 shows the use of the metering rod of FIG. 17 for determining the size of the clear space between the cruciate ligament replacement and the wall of the bore in the femur.

FIG. 18 illustrates, in a representation similar to that of FIG. 1, the use of the metering rod 180 in determining the size of the clear space 138. As can be seen here, the distal end 186 of the metering rod 180 is pushed under pressure as far as possible into the clear space 38. The operator then repeats that procedure with several metering rods of different end diameters $D_M$, if necessary.

In addition to its function as measuring means, the metering rod 180 acts in this case as a dilator, i.e. it simultaneously serves for expanding the clear space 38. This allows the operator to determine the size of the clear space 38, taking into account the expansion that will occur during insertion of the peg 42, 44.

Figure 19:
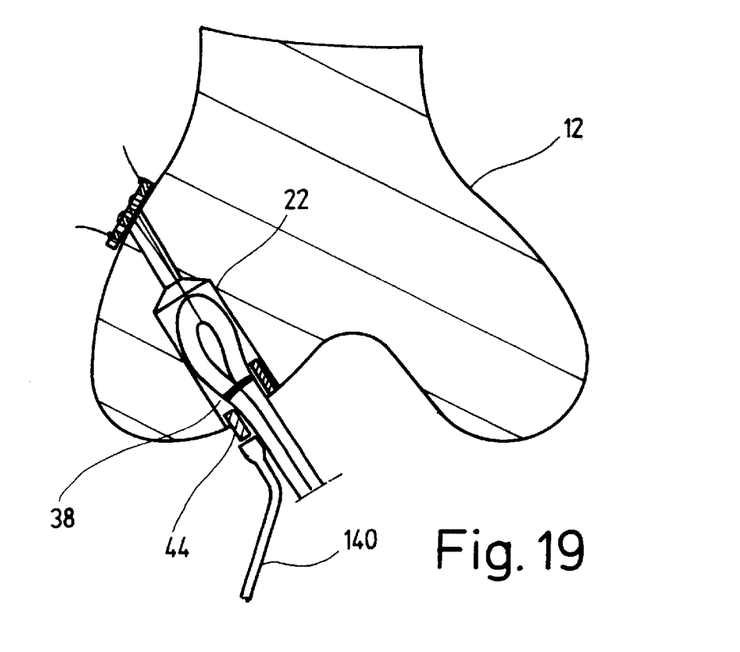
FIG. 19 shows the application of the tamping tool according to the invention as illustrated in FIG. 14.

FIG. 19 illustrates the use of the tamping tool 140, in a representation corresponding to that of FIG. 1. The tamping tool 140 is used after the step of inserting the peg 44, in order to press the peg 44 as far as possible into the clear space 38.

The overall method underlying the present invention therefore comprises the following steps:

Producing a cruciate ligament replacement 16, preferably with the aid of a section of the semitendinosus tendon folded over to a loop 20;

drilling a blind bore 22 into the distal end of the femur 12, and a through-bore 26 into the proximal end of the tibia;

inserting and fixing the cruciate ligament replacement 16 in the blind bore 20 and the through-bore 26 with the aid of anchoring means 30, 32 and 34, 36, respectively;

determining the size of the clear spaces 38, 40 between the cruciate ligament replacement 16 and the walls 37, 39 of the blind bore 22;

shaping one or more pegs 42, 44 to be inserted, preferably from the spongiosa obtained when drilling the blind bore 22 and/or the through-bore 26;

inserting the pegs 42, 44 into the clear spaces 38, 40; and pressing the peg 42, 44 further into the clear space 38, 40.

The method underlying the present invention is of particular advantage in cases where, as has been described above, a section of the semitendinosus tendon is used as a cruciate ligament replacement 16. This is so because it is mainly in this case that the cruciate ligament replacement 16 is folded over in the form of a loop 20.

The step of inserting pegs in existing clear spaces and, correspondingly, the instrumentarium according to the invention may of course also be used in cases where a section of the patellar tendon or a synthetic cruciate ligament graft is used as cruciate ligament replacement 16. In addition, it is understood that in principle pegs made from synthetic materials may also be inserted into the described clear spaces 38, 40.

What is claimed is:

1. An instrumentarium for implanting a cruciate ligament replacement in a knee joint comprising an applicator for inserting a peg into a bore in a bone, into which bore said cruciate ligament is received, said peg being inserted into a clear space between said cruciate ligament replacement and a wall of said bore in said bone, said applicator having a hollow shaft, open at its distal end, a push-rod disposed in said hollow shaft, an operating element connected to said push-rod for moving said push-rod between a first position with a distal end of said push-rod being retracted into said hollow shaft allowing a peg to be inserted into said hollow shaft via open end of said hollow shaft, and a second position for pushing said peg out of said distal open end of said hollow shaft, and a releasable locking mechanism comprising a spring-biased member for fixing said push rod to said hollow shaft in said first position and allowing displacement of said push-rod to said second position when said locking mechanism is released.

2. The instrumentarium of claim 1, wherein said hollow shaft is curved.

3. The instrumentarium of claim 2, wherein said hollow shaft is curved regularly over its length.

4. The instrumentarium of claim 1, wherein said hollow shaft is substantially straight over a central portion and is then bent off in one direction near a distal end of said hollow shaft.

5. The instrumentarium of claim 1, wherein said hollow shaft is straight over its full length.

6. The instrumentarium of claim 1, wherein said push-rod comprises a thickened section at its distal end and a central section, an outer diameter of said thickened section corresponding to an inner diameter of said hollow shaft, and an outer diameter of said central section being smaller than said outer diameter of said thickened section.

7. The instrumentarium of claim 1, wherein said push-rod comprises a thickened section at its distal end, said thickened section is fully positioned within said hollow shaft in said first position of said push-rod at a distance from said opening allowing insertion of a peg over its entire length, and said thickened section projects beyond said distal open end of said hollow shaft in its second pushed-out position.

8. The instrumentarium of claim 1, wherein said operating element can be operated along a longitudinal operating axis extending along said hollow shaft, and a cross-section plane of an opening at said distal open end of said hollow shaft is arranged at an angle related to said operating axis, said angle is less than 90°.

9. The instrumentarium of claim 8, wherein said angle is between 0° and 45°.

10. The instrumentarium of claim 1, wherein said operating element comprises a handle at a proximal end of said push-rod, and a counter-handle mounted on said hollow shaft.

11. The instrumentarium of claim 10, wherein said handle is configured as a ring that can be actuated by a thumb.

12. The instrumentarium of claim 1, wherein said push-rod can be fully withdrawn from said hollow shaft.

13. The instrumentarium of claim 1, wherein said spring-biased member comprises a lever, an end of said lever carries a lug engaging into an annular groove provided in said push-rod, if said push-rod is in a locked condition locked via said locking mechanism.

14. The instrumentarium of claim 1, wherein a plurality of applicators are provided having hollow shafts with different inner diameters.

15. The instrumentarium of claim 1, further comprising a plurality of metering rods for determining a size of said clear space, a distal end of each metering rod corresponding substantially to a shape of said peg to be inserted, and diameters of said distal ends of said metering rods being different one from the other.

16. The instrumentarium of claim 15, wherein each metering rod is provided at its distal end with at least one visible mark arranged at a certain distance from said distal end of said metering rod.

17. The instrumentarium of claim 1, further comprising at least one tamping tool for pressing a peg into said clear space.

18. The instrumentarium of claim 17, wherein said tamping tool is provided with a dished impact surface at its distal end.

19. The instrumentarium of claim 18, wherein said tamping tool is provided with a visible mark at its distal end at a given distance from said impact surface.

20. The instrumentarium of claim 19, wherein a plurality of tamping tools with different diameters of its distal end are provided.

21. The instrumentarium of claim 1, further comprising a pair of pressure forceps for shaping said pegs.

22. The instrumentarium of claim 1, further comprising a pair of pressures forceps for shaping said pegs, said forceps having jaws enclosing between them in a closed condition a circular opening.

23. The instrumentarium of claim 1, further comprising a pair of pressure forceps for shaping said pegs, said forceps having jaws enclosing between them in a closed condition an elliptic opening.

24. The instrumentarium of claim 1, further comprising pair of pressure forceps for shaping said pegs, said forceps having jaws enclosing between them in a closed condition a cylindrical space.

25. The instrumentarium of claim 1, further comprising a pair of pressure forceps for shaping said pegs, said forceps having jaws enclosing between them in a closed condition a conical space.

26. The instrumentarium of claim 1, further comprising a hollow chisel by means of which bone material of said bone can be removed for shaping a bore.

27. The instrumentarium of claim 1, further comprising a core drill by means of which bone material can be removed from said bone for shaping a bore.

* * * * *